United States Patent [19]

Schuurman et al.

[11] 4,359,448

[45] Nov. 16, 1982

[54] FLUIDIZED BED REACTOR FOR EXOTHERMIC REACTIONS

[75] Inventors: Pieter J. Schuurman; Marius B. Teekens, both of The Hague, Netherlands

[73] Assignee: Shell Oil Company, Houston, Tex.

[21] Appl. No.: 244,462

[22] Filed: Mar. 16, 1981

[30] Foreign Application Priority Data

Apr. 15, 1980 [NL] Netherlands .......................... 8002172

[51] Int. Cl.³ ........................... F27B 15/16; B01J 8/44
[52] U.S. Cl. ................................ 422/143; 165/104.16; 422/49; 422/146; 422/201
[58] Field of Search .................. 422/49, 143, 146, 200, 422/201; 431/7, 170; 122/4 D; 110/245; 165/104.16; 34/57 A; 432/15, 58; 201/31

[56] References Cited

U.S. PATENT DOCUMENTS

| 2,518,270 | 8/1950 | Barr | 422/201 X |
| 2,594,330 | 4/1952 | Mayhew | 422/201 X |
| 2,664,346 | 12/1953 | Mayhew | 23/288 |
| 2,852,545 | 9/1958 | Jenny | 422/146 X |
| 4,060,127 | 11/1977 | Savin et al. | 165/145 |
| 4,226,830 | 10/1980 | Davis | 422/143 |

Primary Examiner—Barry Richman
Attorney, Agent, or Firm—Dean F. Vance

[57] ABSTRACT

A reactor for exothermic reactions provided with bundles of narrow axial cooling pipes, mounted between distributing and collecting drums ("steam headers") provided with tube sheets. The distributing drums are placed symmetrically around the outlet end of a central axial coolant inlet pipe, recovering from top to bottom of the reactor. A feed gas inlet at the bottom branches into feed pipes with a quantity of nozzles, in order to allow the gas to fluidize a mass of catalyst particles.

6 Claims, 2 Drawing Figures

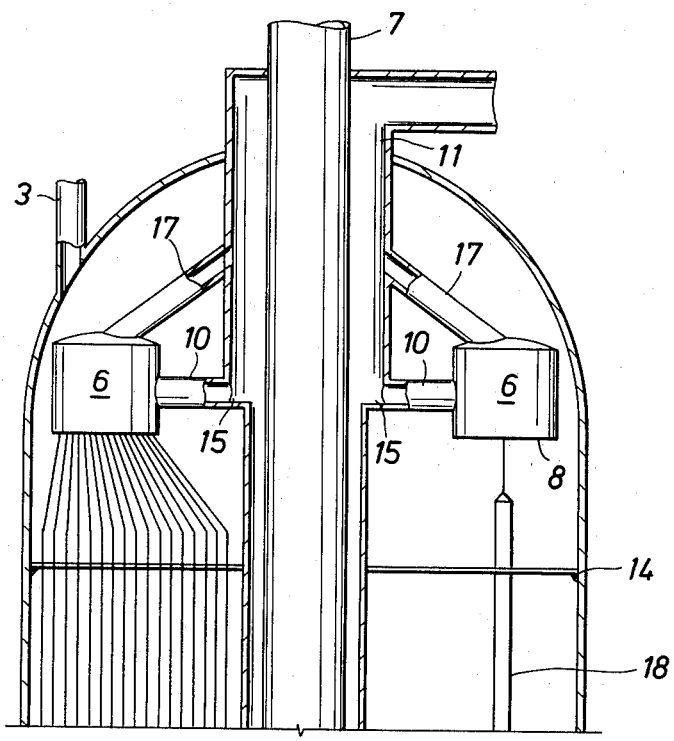
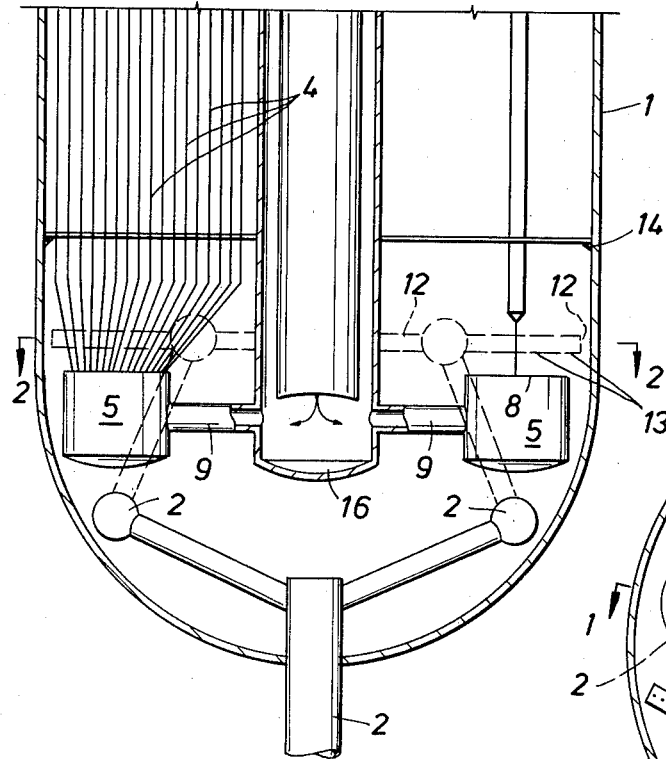
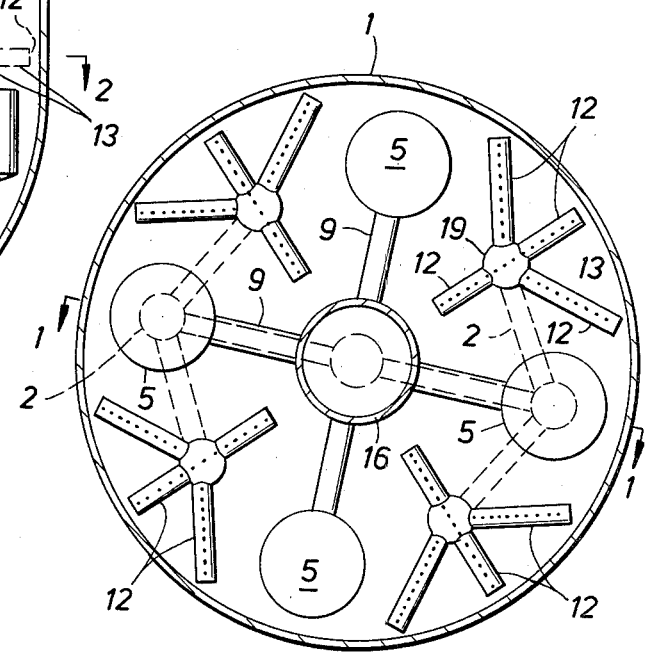
FIG. 1
FIG. 2

FLUIDIZED BED REACTOR FOR EXOTHERMIC REACTIONS

BACKGROUND OF THE INVENTION

1. Field of the Invention

This invention relates to a reactor suitable for carrying out exothermic reactions in either the gaseous or the vapor phase. More particularly, the invention deals with a reactor having internal cooling pipes.

2. Description of the Prior Art

Reaction vessels having internal cooling tubes are known, for example, from U.S. Pat. No. 2,664,346. These reactors serve the same function as shell and tube heat exchangers, i.e., the removal of heat (e.g. the exchanger of U.S. Pat. No. 4,060,127), plus serving as the reaction vessel. However, larger reactors are required than in the past, not only because all chemical processes are carried out on a larger scale but also because certain processes are being increasingly used, in particular the synthesis of hydrocarbons. One such process for the preparation of hydrocarbons is the conversion of carbon monoxide and hydrogen prepared by the gasification of coal.

It has been found that it is not feasible just to scale up the past reactors, such as the reactor of U.S. Pat. No. 2,664,346, to increase the capacity, as the reactor then becomes less suitable for the purpose envisaged for the following reasons. In the first place the wall strength poses a problem in the case of larger diameters since the wall thickness must be increased and the construction becomes increasingly heavier. In the second place it is desired to have as few as possible penetrations in the shell in view of the high pressures which occur. In the reactor of U.S. Pat. No. 2,664,346 one pipe from each header space and from each manifold space passes through the shell. In addition, as a result of the larger dimensions, the thermal expansion and in particular the stress due to unequal expansion may pose a problem. Finally it becomes difficult, when using larger diameters, to achieve uniform distribution of the gaseous reaction media over the full diameter of the reactor, in particular if—as in the U.S. Pat. No. 2,664,346 reactor—the reaction media enter the reactor centrally at the bottom. In order to make full use of the entire catalyst mass and of the complete cooling surface available, uniform distribution is required. Besides, it is impossible in the U.S. Pat. No. 2,664,346 reactor to negotiate internal access to the cooling tubes for maintenance or inspection without completely dismantling it.

SUMMARY OF THE INVENTION

According to the invention it has now been found that the problems noted above are solved by providing the header and manifold spaces, which are regularly arranged around an axial supply pipe for the coolant, with flat tube sheets toward which the tubes of a bundle converge and to which they are connected, by connecting the manifold spaces to the supply pipe by means of radial pipes and likewise the header spaces by means of radial pipes with a coolant discharge pipe arranged concentrically around the supply pipe and by branching the inlet pipe or pipes in a stellate configuration so that the branches are between or just downstream of the manifold spaces and by providing each of these branches with a number of gas outflow openings which are suitable to keep in the fluidized state during operation a finely grained mass of catalyst particles present in the reactor.

In particular, the present invention relates to a reactor suitable for carrying out exothermic reactions in the gaseous phase or the vapor phase, the reactor being of the type provided at the bottom with one or more inlet pipes for gaseous reaction media and at the top with one or more outlet pipes for reaction product and provided with a number of bundles of parallel axial tubes for a coolant to be passed through the reactor co-currently with the reaction media, which tubes are throughout the greater part of their length substantially uniformly distributed over the cross-section of the reactor, the tubes of each bundle being connected to a header and manifold space. As a rule such a reactor is cylindrical, the cylinder axis being at least substantially vertical and provides spaces for accommodating a catalyst mass.

The reactor wall is no longer weakened by a large number of penetrations for the passage of coolant since the coolant is supplied through one large axial supply pipe and is discharged through a discharge pipe concentrically arranged around the supply pipe. The large relatively cool supply pipe which extends from the top to the bottom of the reactor also imparts rigidity to and supports the thin tubes of the bundles, so that the latter are not elongated under the effect of their own mass and the high temperature during operation. The cooling parts of the reactor are solely suspended at the top from a kind of yoke and may consequently freely expand and contract in an axial and radial direction. During operation the thin cooling tubes will obviously expand somewhat more than the central supply pipe as a result of their higher temperature, although this effect is not harmful since the curves of the thin tubes in the vicinity of the header and manifold spaces are capable of accommodating the longitudinal expansion.

Since only one supply pipe and one outlet pipe for the coolant are present, they are so large that their interior is accessible. It has now become possible to gain access to the header and manifold spaces and—if required—to check certain tubes or complete bundles for leakage, to seal them or to carry out other maintenance operations without dismantling.

The uniform distribution of the gaseous reaction media over the entire width of the reactor is finally ensured by the stellate inlet pipe(s) present in the space formed by the converging of coolant tubes toward the manifold spaces, which tubes are otherwise uniformly distributed over the cross-section of the reactor.

Preferably, one or more grids are provided between the header and the manifold spaces which grids are provided with openings for the passage of the cooling tubes and throughflow of reaction media. These grids maintain the distance between the cooling tubes which tend to buckle slightly during operation as a result of the relatively high temperature. The grids do not impede transfer of the gases present nor the sustaining of the fluidized bed. These grids are preferably divided into a number of sectors the number of which is equal to the number of header or manifold spaces. By sectors are here meant geometrical sectors of a circle with the proviso that an orifice is present at the center of the circle to allow for the central coolant supply pipe. This divided arrangement offers certain advantages from the assembly and maintenance point of view.

The axial supply pipe is preferably surrounded by a second concentric pipe one extremity of which is connected to the lower extremity of the coolant discharge pipe, the other extremity debouching with the supply pipe into a space to which the radial pipes leading to the manifold spaces are connected. In other words, this second concentric pipe annularly surrounds the supply pipe from the radial pipes running to the header spaces at the top down to the radial pipes running to the manifold spaces at the bottom of the reactor. This annular pipe serves for the recirculation of unvaporized coolant. The header spaces act as vapor/liquid separators; the liquid (mostly water) runs along the bottom of the radial tubes to the annular recirculation pipe, the vapor (mostly steam) disappears via the top lip of the radial pipes into the discharge pipe.

In order to augment the discharge capacity and the mechanical rigidity and to improve the liquid/vapor separation it is preferred to install a second, more or less radial discharge tube pipe between the top of each header space and the central discharge pipe, so that each header space is connected to the discharge pipe by two superposed at least essentially radial pipes. Most vapor will then pass through the upper pipe, most liquid through the lower one.

In order to impart extra rigidity to the suspension construction of the cooling tubes, the central tube of each bundle of cooling tubes is preferably heavier than the other tubes of the said bundle. This central tube bears the greater part of the weight of the manifold spaces and accommodates stresses caused by unequal thermal expansion. The thin cooling tubes could otherwise be permanently buckled or elongated. It will be possible for thermal expansion to occur without giving rise to unacceptable stresses, as elongation merely causes the existing curvatuve to become more pronounced.

The number of tube bundles may not be too small since too large a number of cooling tubes would then be suspended from the tube sheet of each header space, which would result in the tube sheet having to be made unacceptably heavy. Calculations show that if in a reactor having a diameter of 4 meters (m), all tubes are allowed to run from one tube sheet, the required wall thickness of that tube sheet would exceed 0.5 m On the other hand, it is not possible to have too many tube bundles because construction and maintenance would become too complicated while too little space would remain between the manifold spaces for the stellate branches of the gas inlet pipe(s). For this reason the number of tube bundles in actual practice is preferably 4–12.

BRIEF DESCRIPTION OF THE DRAWING

The invention will now be further explained with reference to the drawing.

FIG. 1 is a diagrammatic axial cross-section of a preferred embodiment of a reactor according to the invention.

FIG. 2 is a vertical cross-section taken on line II—II of FIG. 1. For the sake of clarity the manifold spaces and the radial tubes have not been shown in FIG. 2 as broken lines but as continuous lines. In this form a reactor may have a diameter of 10 m or more.

DETAILED DESCRIPTION OF THE DRAWING

The figures show a reactor having a wall (1), an inlet pipe (2) and an outlet pipe (3) for gases. The inlet pipe (2) branches several times and finally issues into a manifold (19) to which stellate branches (12) are connected. Each of these is provided with gas outflow openings (13) which are suitable for maintaining in the fluidized state during operation a finely grained mass of catalyst particles (not shown in the Figure) present in the reactor. During operation a coolant, for example boiling water under pressure, flows through a supply pipe (7) via a space (16) and radial pipes (9) to manifold spaces (5). These manifold spaces are hemispherical in shape in order to withstand the pressure difference across the interior and exterior of the space as well as possible with as little material as possible. A number of cooling tubes (4) are connected to flat tube sheets (8) which tube diverge in the direction of the top of the reactor, so that they are uniformly distributed over the cross-section of the reactor for the greater part of their length. In a reactor of some size, i.e., a reactor having a cross-section of several m, many thousands of tubes (4) are arranged, in this instance bundled into four bundles. Grids (14) are present at various levels in the reactor which grids keep the tubes equidistantly spaced, for example 1–5 times the external diameter. A tube (18) occupying a central position in each bundle of tubes (4) imparts extra rigidity to the construction. For the sake of clarity one tube (18) is shown in FIG. 1 without the adjacent tubes (4).

In the top of the reactor the cooling tubes converge again to a number of tube sheets (8) of likewise hemispherical header spaces (6). In the header spaces the vapor separates from the liquid. The vapor mainly disappears through a pipe (17) into the central discharge pipe (11). The greater part of the liquid returns via a radial pipe (10) to the header spaces through the central annular pipe which connects the bottom extremity (15) of the discharge pipe (11) with the space (16).

The reactor according to the invention is suitable for all kinds of reactions in which heat has to be exchanged, and may optionally even be used purely as a heat exchanger. It is particularly suitable for exothermic catalytic reactions, such as the water gas shift reaction, the synthesis of methanol, reforming of methanol, methanation of synthesis gas to form a substitute for natural gas and various petrochemical processes. More in particular, the reactor is suitable for the synthesis of hydrocarbons from synthesis gas to form a substitute for petroleum.

What is claimed is:

1. A reactor provided at the bottom with one or more pipes for gaseous reaction media and at the top with one or more outlet pipes for reaction product, which reactor is provided with a number of bundles of parallel axial tubes for a coolant to be passed through the reactor concurrently with the reaction media, means maintaining said tubes for the greater part of their length substantially uniformly distributed over the cross-section of the reactor, the tubes of each bundle being connected to a header and manifold space located within the reactor, said header and manifold, which being regularly arranged around an axial supply pipe for the coolant, are provided with flat tube sheets toward which the tubes of a bundle converge and to which they are connected, said manifold spaces are connected to the supply pipe by means of radial pipes and the header spaces are also connected by means of radial pipes with a coolant discharge pipe arranged concentrically around the supply pipe, said concentrically arranged axial supply pipe and said coolant discharge pipe passing through a wall of said reactor, said inlet pipe or pipes are branched in a stellate configuration so that the branches are between or just downstream of the manifold spaces and said branches are each provided with a number of gas outflow openings which are suitable to keep in the fluidized state during operation a finely grained mass of catalyst particles present in the reactor, wherein said axial supply pipe is surrounded by a second concentric pipe one extremity of which is connected to the lower extremity of the coolant discharge pipe, the other extremity debouching with the supply pipe into a space to which the radial pipes leading to the manifold spaces are connected.

2. A reactor as claimed in claim 1, wherein each header space is connected to the discharge pipe by two superposed, at least essentially radial pipes.

3. A reactor as claimed in claim 1, wherein the central tube of each bundle of cooling tubes is heavier than the other tubes of that bundle.

4. A reactor as claimed in claim 1, wherein the number of tube bundles is 4–12.

5. A reactor as claimed in claim 1, wherein said uniform distribution maintaining means includes one or more grids arranged between said manifold and header spaces which grids are provided with openings for the passage of the cooling tubes and throughflow of reaction media therethrough.

6. A reactor as claimed in claim 5, wherein said grids are divided into a number of sectors which number is equal to the number of manifold or header spaces.

* * * * *